(12) United States Patent  
Consigny

(10) Patent No.: US 6,203,487 B1
(45) Date of Patent: Mar. 20, 2001

(54) USE OF MAGNETIC PARTICLES IN THE FOCAL DELIVERY OF CELLS

(75) Inventor: P. Macke Consigny, Cherry Hill, NJ (US)

(73) Assignee: Thomas Jefferson University, Philadelphia, PA (US)

(*) Notice: Subject to any disclaimer, the term of this patent is extended or adjusted under 35 U.S.C. 154(b) by 0 days.

(21) Appl. No.: 09/224,504

(22) Filed: Dec. 31, 1998

Related U.S. Application Data

(60) Provisional application No. 60/070,281, filed on Dec. 31, 1997.

(51) Int. Cl.[7] ........................................ A61N 2/00
(52) U.S. Cl. ................................................ 600/12
(58) Field of Search ................... 600/12, 13, 14, 600/420, 431; 128/897, 898, 899

(56) References Cited

U.S. PATENT DOCUMENTS

| | | | | |
|---|---|---|---|---|
| 3,592,185 | * | 7/1971 | Frei et al. | 600/431 |
| 4,106,488 | * | 8/1978 | Gordon | 128/898 |
| 4,136,683 | * | 1/1979 | Gordon | 600/12 |
| 4,269,826 | * | 5/1981 | Zimmerman et al. | 600/12 X |
| 4,652,257 | * | 3/1987 | Chang | 600/12 X |
| 5,067,952 | * | 11/1991 | Gudov et al. | 600/12 X |
| 5,087,438 | * | 2/1992 | Gordon | 600/10 X |
| 5,129,877 | * | 7/1992 | Gallo et al. | 600/12 |
| 5,236,410 | * | 8/1993 | Granov et al. | 600/12 |
| 5,441,507 | * | 8/1995 | Wilk | 128/898 X |
| 5,655,546 | * | 8/1997 | Halpern | 128/898 |
| 5,921,244 | * | 7/1999 | Chen et al. | 128/897 |

OTHER PUBLICATIONS

Yeh et al., "Intracellular Labeling of T–Cells with Superparamagnetic Contrast Agents" *Magnetic Resonance in Medicine* 30(5):617–625 (1993).

Yeh et al., "In Vivo Dynamic MRI Tracking of Rat T–Cells Labeled with Superparamagnetic Iron–Oxide Particles" *Magnetic Resonance in Medicine* 33(2):200–208 (1995).

Krieg et al., "Superparamagnetically labeled neutrophils as potential abscess–specific contrast agent for MRI", *Magnetic Resonance Imaging* 13(3):393–400 (1995) (PubMed abstract only).

* cited by examiner

*Primary Examiner*—Samuel G. Gilbert
*Assistant Examiner*—Joseph A. Cadugan
(74) *Attorney, Agent, or Firm*—Clifford K. Weber, Esq.; Janet B. Smith

(57) ABSTRACT

A method for focal delivery of cells to a target tissue in an animal is provided wherein magnetic particles are inserted into cells and then administered into an animal. Focal delivery is accomplished by placement of a magnetic field around or adjacent to the target tissue to which the cells are to be delivered.

22 Claims, 1 Drawing Sheet

USE OF MAGNETIC PARTICLES IN THE FOCAL DELIVERY OF CELLS

This application claims benefit of Application Provisional 60/070,281, filed Dec. 31, 1997.

BACKGROUND OF THE INVENTION

Local delivery of therapeutics to the site of action in the body is often desired. For example, bronchodilator drugs are most effective when inhaled directly into the lungs, avoiding systemic circulation which can lead to rapid metabolism of compounds as well as effects at tissues other than the target sites. In the same way, targeted or focal delivery of cells, as part of a therapeutic regimen, would be useful to avoid potential side effects of cell treatment as well as metabolism by the body.

Accordingly, focal delivery of cells in the human body has been an active area of research. Cells have been explored as means of gene transfer to the brain, instead of viral vectors (Taylor, R., 1997 Neuromuscul. Disord., 7:343–351); neural precursor cells containing genes encoding deficient enzymes were transplanted into mouse models of neurodegenerative disease. Engineered urothelial cells have also been locally implanted to produce a functional neo-organ (Yoo, J. J. and A. Atala, 1997 J. Urol., 158:1066–1070). Encapsulated genetically engineered cells that continuously released ciliary neurotrophic factor have also been tested in humans and animals (Tan, S. A. et al., 1996 Cell Transplant., 5:577–587).

Paramagnetic particles and paramagnetic techniques are used in medicine in a variety of ways. For example, paramagnetic contrast media have been described by Catalano, C. et al., 1995 Radiol. Med., 89:825–830; Jackler, R. K. et al., 1990 Otolaryngol. Head Neck Surg., 102:70–77; and Bonnet, P. A. et al., 1990 Magn. Reson. Imaging, 8:71–77. A hepatocyte-specific contrast media that allows for specific imaging of hepatitis has also been described by Tanimoto, A. et al., 1993 J. Magn. Reson. Imaging, 3:786–793. Paramagnetic substances are also used in analytical chemical assays.

Internalized magnetic particles have also been used to study inflammation. For example, Yeh et al., 1993 MRM, 30:617–625 and 1995 MRM, 33:200–208, demonstrated that rat T-cells that have internalized dextran-coated iron oxide particles can be used to identify areas of inflammation by magnetic resonance imaging. Similarly, Krieg et al., 1995 Magn. Reson. Imagine, 13:393–400, demonstrated that neutrophils that had previously phagocytosed polystyrene-embedded magnetite micro crystals could be used to identify sites of inflammation on T2-weighted magnetic resonance images.

It has now been found that magnetic particles can be used in the focal delivery of cells. In the present invention, a new method for targeted delivery of cells is provided using magnetic particle-containing cells and a magnetic field which ensures adequate attachment of cells to the target tissue. Once attached, cells and their products are available for local activity.

SUMMARY OF THE INVENTION

An object of the present invention is to provide a method of delivering selected cells to a target tissue in an animal which comprises culturing selected cells so that the selected cells internalize magnetic particles; administering the selected cells containing the internalized magnetic particles to the animal; and placing a magnetic field around the target tissue in the animal so that the selected cells move to the target tissue of the animal and facilitate focal delivery of the cells to the target tissue.

DETAILED DESCRIPTION OF THE INVENTION

There are a variety of situations in medical therapy wherein it is advantageous to provide focal delivery of cells. For example, following balloon angioplasty, half of the procedure failures have been attributed to local damage to the arterial inner surface (Baim, D. S. and W. Grossman, 1994 Harrison's Principles of Internal Medicine, pp. 986–987). Such surface tissue damage results in thrombus formation and tissue spasm. As a result, a method to re-endothelialize the inner surface of the artery following angioplasty provides a means to prevent failure of the procedure. Focal cell delivery can also be used to treat tumors with cells that release cytotoxic or cytostatic factors. With such targeted delivery, tumors can be treated locally, thereby promoting efficacy of treatment and reducing side effects associated with systemic delivery of therapeutics. Other uses of ,focal cell delivery include delivery of genetically modified cells for treatment of diseases such as, but not limited to, respiratory diseases, liver failure, and diabetes.

In the present invention a method is provided for focal delivery of selected cells to a target tissue wherein prior to administering the selected cells, magnetic particles are inserted into the cells either by culturing the cells with magnetic particles under conditions in which the cells internalize the magnetic particles or by manual insertion of the magnetic particles into the cells by known techniques. By "magnetic particle" it is meant to include, but is not limited to, microspheres, conjugates, micelles, colloids, aggregates and complexes of a ferromagnetic, paramagnetic or superparamagnetic material. The selected cells are then administered to the subject and manipulated or directed to the target tissue via a magnetic field located adjacent to the target tissue.

Experiments were performed both in vitro and in vivo to demonstrate the method of the present invention. For in vitro studies, microvascular endothelial cells were isolated from rabbit peri-renal adipose tissue in accordance with methods described by Consigny, P. M., 1997 JVIR 8:595–604. After isolation, the cells were plated on gelatin-coated culture dishes and cultured for two to four passages. After the cells were established in culture, they were exposed to albumin-coated superparamagnetic microspheres (tosylactivated superparamagnetic polystyrene microspheres, 4.5 microns in diameter, M-450 Dynabeads) at a microsphere to cell ratio of 4:1. The endothelial cells were then cultured for an additional 18 hours to allow time for microsphere internalization by phagocytosis.

Figure 1A:
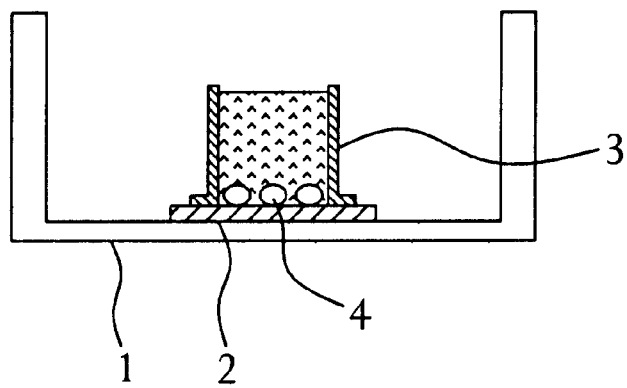
FIG. 1a shows a diagram of a chamber used to measure endothelial cell attachment in the absence of a magnet.
Figure 1B:
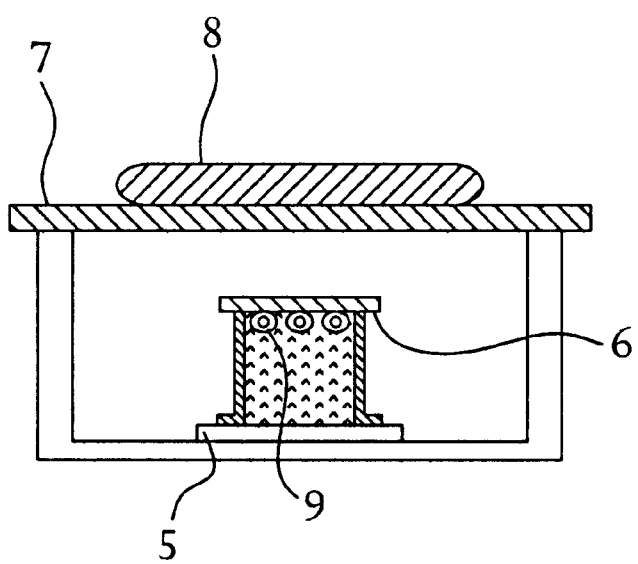
FIG. 1b shows a diagram of a chamber used to measure endothelial cell attachment in the presence of a magnet.

Once prepared, the microsphere-containing cells were used in a static cell adhesion study to determine any negative influences of the presence of paramagnetic microspheres within the cells on endothelial cell adhesion. For these experiments, a special cell adhesion apparatus was used as shown in FIGS. 1a and 1b. This apparatus is constructed of a 35 mm diameter culture dish 1 (Corning Glass Works) which serves as the base, an incubation well constructed from a matrix-coated glass coverslip bottom 2 (No. 1, 18 mm$^2$, Corning Glass Works) attached matrix side up, with petroleum jelly, to the culture dish, and the open end of a cut Eppendorf tube 3 attached to the glass coverslip with petroleum jelly. For experiments in which cell Endothelial cells 4 adhered to matrix coated glass cover slip bottom 2 are shown adhesion was measured in a magnetic field, a modified apparatus (FIG. 1b) was constructed of an uncoated coverslip 5 that served as the bottom of the chamber, a matrix-coated glass coverslip 6 placed matrix side down on the upper rim of the Eppendorf tube, and a glass microscope slide 7 (1"×3", Corning Glass Works) placed on the rim of the culture dish in order to support a neodymium-iron-boron magnet 8 over the chamber. Magnetic particle-containing endothelial cells 9 adhered to matrix coated glass cover slip bottom 6 are shown.

Coverslips were prepared for adhesion experiments by applying 15 μl of a fibronectin solution (1 ∥g/μl of bovine plasma fibronectin) to the upper surface of each coverslip to coat the coverslip and then allowing the coverslips to air dry. Each coverslip was then rinsed with a media composed of equal volumes of Dulbecco's minimal essential media and F12 media (DME/F12), treated for 30 minutes with a solution of 1% bovine serum albumin (BSA) in DME/F12 to block nonspecific binding sites, and rinsed with DME/F12 again. After the coverslips were prepared, the endothelial cells were detached from their culture dishes by replacing the culture media in each dish with a solution containing 1% BSA and EDTA (2 mM) and giving the dish occasional, brief shakes. The detached endothelial cells were then isolated by centrifugation and resuspended in culture media at a concentration of $1\times10^5$ cells per milliliter.

For the adhesion experiments, 25,000 endothelial cells were added to each chamber, and the chamber assembly was placed in a 37° C. humidified cell culture incubator. After permitting time for cell adherence for 5, 10, 15, or 30 minutes, the assembly was removed from the incubator, non-adherent cells were removed from each chamber with repeated washing, and adherent cells were fixed by the addition of 2% glutaraldehyde. After allowing 15 minutes for fixation, each matrix-coated coverslip was removed from its chamber assembly, immersed in a 2% solution of toluidine blue, for staining, rinsed in tap water, allowed to air dry, and then examined under a microscope. The cells in 40 fields (at 500×) were counted, the counts for two coverslips were averaged, and the results were expressed as a percent of the cells adherent after 30 minutes in which time maximal cell adhesion to fibronectin occurs.

Experiments were then performed to determine the influence of microsphere internalization on cell adhesion under the influence of gravity alone Control or microsphere-containing endothelial cells were added to chambers and cell adhesion was measured and compared. Under the influence of gravity, the adhesion of normal endothelial cells was time dependent, increasing from 34% after a 5 minute attachment period to 74%, 70%, and 100% after attachment periods of 10, 15, and 30 minutes, respectively. Similar adhesion results were obtained for the microsphere-containing endothelial cells under the influence of gravity. Cell adhesion averaged 40, 56, 93 and 100% after attachment periods of 5, 10, 15, and 30 minutes, respectively.

Experiments were then performed to determine the effect of magnetic levitation on the adhesion of microsphere-containing endothelial cells. For these experiments, the chambers were assembled with uncoated glass coverslip bottoms. Microsphere-containing endothelial cells were then added to each chamber, culture media was added to completely fill the chamber, a matrix-coated glass coverslip was placed, matrix-side down, on the chamber in contact with the culture media, a one inch diameter neodynium-iron-boron magnet supported by a glass slide was placed above the chamber to levitate the cells, and the chamber was placed in the incubator. Cell adhesion was then measured after 5, 10, 15, or 30 minutes. The results of these experiments were then compared to results from experiments wherein adhesion was measured under the influence of gravity alone.

Under the influence of the magnetic field, the adhesion of microsphere-containing endothelial cells was also time dependent and was similar to adhesion of normal endothelial cells under the influence of gravity alone. Microsphere-containing endothelial cell adhesion averaged 75, 86, and 100% for attachment periods of 10, 15, and 30 minutes. However, for the 5 minute attachment period, the adhesion of the microsphere-containing endothelial cells was significantly greater than for normal endothelial cells (69% versus 34%; $p<0.05$).

Upon completion of the static adhesion experiments, the toluidine blue-stained coverslips were examined microscopically and the number of microspheres in each of 100 cells was determined so that the frequency distribution of magnetic microspheres per cell for cells adherent under the influence of gravity alone could be compared to the distribution for cells adherent in a magnetic field. Results showed that the distributions were similar for cells containing three or more microspheres. However, microsphere-containing endothelial cells containing one or two microspheres were found in greater number when adhesion was under the influence of gravity alone.

Dynamic cell adhesion experiments were also performed to determine the effect of the internalization of superparamagnetic microspheres on the ability of the cells to resist removal from a matrix by a shear stress. In these experiments, normal or microsphere-containing endothelial cells were placed on glass microscope slides previously coated with fibronectin (0.6 $\mu$/cm$^2$). Each slide was then placed in a humidified incubator for 5, 10, 15, or 30 minutes to permit cell adhesion. Afterwards, the slide was transferred to a parallel plate apparatus which was then placed on the stage of an inverted microscope and attached to a perfusion pump. Prior to initiating fluid flow, a video image of the endothelial cells in a 2 mm$^2$ area viewed through a 4× objective was captured by a CCD video camera linked to a video frame grabber under the control of a computer. After the control image was captured, the endothelial cells were exposed to a shear stress of 25 dynes/cm$^2$ for two minutes by pumping DME/F12 media through the chamber. A second video image was captured. Upon completion of the experiment, the endothelial cells in each video image were counted, and the results expressed as a percentage of the cells present in the image captured prior to the exposure to shear stress in order to normalize for differences in the number of cells in the initial video image.

The fluid shear stress (t, dynes/cm$^2$) in the parallel plate chamber was calculated according to the equation $t=6$ Qm/bh$^2$ where Q is the flow rate (ml/min), m is the viscosity of the perfusate (0.007 poise), b is the width of the flow channel (2.5 cm), and h is the height of the flow channel (0.0118 cm).

Upon completion of the shear stress experiments, cells that were adherent to the glass slides were fixed by immersion in 2% glutaraldehyde, stained by immersion in a 2% toluidine blue solution, and examined by light microscopy to determine the number of microspheres in each of 100 adherent cells. The resulting frequency distribution was then compared to the distribution obtained from an identical analysis performed on superparamagnetic microsphere-containing endothelial cells that had adhered to fibronectin-coated glass slides for four hours in the absence of a shear stress.

Results showed that fractions of endothelial cells that remained attached to fibronectin-coated glass slides after exposure to a shear stress of 25 dynes/cm$^2$ were directly related to the time allowed for cell adhesion. For normal endothelial cells containing no microspheres, the percentage of cells that remained adherent after attachment periods of 5, 10, 15, and 30 minutes were 32, 49, 75, and 82% respectively. For the same adhesion times, the percentages of microsphere-containing endothelial cells that remained adherent were 42, 33, 56, and 69% respectively. These latter percentages were not significantly different from those for the normal endothelial cells except at 30 minutes when adhesion of the microsphere-containing endothelial cells was significantly less than normal ($p<0.05$). The loss of microsphere-containing endothelial cells after exposure to shear stress was not influenced by the number of microspheres contained within the cells, since there was no difference in the frequency distributions for cells that remained adherent after exposure to a sheer stress of 25 dynes/cm$^2$ or the cells that had been allowed to adhere for four hours but were not exposed to a shear stress.

Experiments were also performed on two rabbits to determine whether the method of the present invention would lead to circumferential placement of endothelial cells after balloon dilation of iliac arteries. A mixture of normal and microsphere-containing cells were employed to cover gravity-dependent and gravity-independent arterial surfaces.

Before placement into rabbits, the endothelial cells were prepared as described above, beginning two days before cell delivery. On the day of cell delivery, the two groups of cells were removed from their culture dishes. The superparamagnetic-containing cells were isolated with a magnet and the two groups were stained with the fluorescent dye PKH26. After staining, the cells were washed, resuspended in culture media, and mixed together in a final volume of 2 ml.

While the endothelial cells were being stained, the rabbit was prepared for balloon angioplasty and interventional re-endothelialization. Each rabbit was anesthetized with an intramuscular injection of a mixture of ketamine and xylazine. The rabbit was strapped in a supine position in a semicircular support device that permitted the rabbit to be rotated axially 60 degrees in either direction. A femoral artery was then surgically isolated, an angioplasty balloon catheter (3 mm×2 cm) was inserted through a femoral arteriotomy and advanced into the external iliac artery under fluoroscopic guidance, and heparin (200 U/kg) was administered intra-arterially. Balloon angioplasty of the artery was then performed twice, one minute per dilation, at an intraballoon pressure of 8 atmospheres.

Upon completion of the balloon dilatation, the angioplasty balloon catheter was removed and replaced with an endothelial cell delivery catheter (Medi-Tech, Boston Scientific; Consigny, P. M., 1997 *JVIR* 8:595–604). The end of this delivery catheter was comprised of two balloons that, when inflated, isolated a 1.5 cm long segment of artery. Between the two balloons, the shaft of the catheter had two openings connected to separate lumina that were used for the infusion of endothelial cells and the withdrawal of fluid and cells.

For endothelial cell delivery, the more central balloon was inflated first and saline was infused to displace the blood in the artery. The more distal balloon was then inflated and tissue culture media was infused into the interballoon space to displace any residual blood. Re-endothelialization was then begun with the slow infusion of a one milliliter aliquot of endothelial cells. After delivery of the cells, a neodynium-iron-boron magnet (2"×2"×0.5" thick) was placed on the abdomen directly over the artery and taped in place. After allowing the cells to attach for 15 minutes, the rabbit was rotated axially 60 degrees and a 0.5 ml aliquot of endothelial cells was slowly infused. After allowing an additional 15 minutes for attachment, the rabbit was rotated axially 120 degrees in the opposite direction and a final 0.5 ml aliquot of cells was slowly infused.

Upon completion of the 45 minute re-endothelialization procedure, the re-endothelialized artery was removed for histologic analysis. For quantitation of re-endothelialization, each cross-section of artery was examined with a fluorescence microscope to determine the endoluminal distribution of the fluorescently labeled endothelial cells. Specifically, each cross-section was visually divided into eighths and one-eighth of the circumference was visually examined. The cross-section was assigned a score of 0 if no endothelial cells were present, 1 if less than 50% of the luminal surface was covered with endothelial cells, and 2 if more than 50% of the luminal surface was covered with endothelial cells.

Of the 192 areas (8 areas per arterial cross section×24 cross-sections per artery, one artery per rabbit) examined, results showed that the re-endothelialization scores for the two rabbits were similar. The average scores for rabbit 1 and 2 were 1.21 and 1.13, respectively. The distribution of scores were also similar. In rabbit 1, 11% of the areas had a score of 0, 65% had a score of 1, and 24% had a score of 2. In rabbit 2, 11% had a score of 0, 57% had a score of 1, and 32% had a score of 2. The areas covered by normal endothelial cells were 67% for rabbit 1 and 53% for rabbit 2, while the areas covered by microsphere-containing endothelial cells were 22% for rabbit 1 and 36% for rabbit 2. Most importantly, the endothelial cells were deposited circumferentially.

These data show that focal delivery of selected cells to a selected tissue, in this example for interventional re-endothelialization, is possible using the method of the present invention. As demonstrated herein, by focally delivering paramagnetic microsphere-containing cells to the arterial surface, and placing a magnetic field over the artery, the cells can be manipulated. The microsphere-containing endothelial cells are levitated onto the gravity-independent portion of the artery by the magnet placed externally over the artery. Normal endothelial cells were allowed to gravitate onto the gravity-dependent portion of the artery.

Further, little to no toxicity has been reported from long-term exposure to superparamagnetic microspheres. Injection into mice of as many as $2\times10^8$ of the same superparamagnetic microspheres used in the present invention resulted in no acute or chronic effects over 8 months time. No inflammatory reactions were observed even in the liver where the microspheres were present in dense clusters.

The method of the present invention is applicable to any cell type that can internalize magnetic particles or into which magnetic particles can be placed. Cells can be normal or genetically modified and can be either free or encapsulated in a matrix. Prior to delivery of cells containing the magnetic particles, a magnet is placed adjacent to a target tissue, i.e., an area of the body or a selected tissue or organ into which local cell delivery is desired. The magnet can be positioned superficial to the body surface or can be placed internal to the body surface using surgical or percutaneous methods inside or outside the target tissue for local delivery. The magnetic particle-containing cells are then delivered either by direct injection into the selected tissue or to a remote site and allowed to passively circulate to the target site or be actively directed to the target site with a magnet. Delivery can be made via an injection needle, a catheter or other acceptable delivery device. If local delivery requires circumferential cellular coverage, the structure to be covered is placed horizontally and a magnet is placed above the target tissue. A mixture of magnetic particle-containing cells and normal cells are then delivered in order to cover gravity independent and gravity dependent areas, respectively. Gravity-dependent cell coverage can be further improved by rotating the structure axially to increase gravity-dependent surface area. Alternatively circumferential coverage is obtained by surrounding the target tissue with magnets and delivering only magnetic particle-containing cells.

Accordingly, the method of the present invention is useful in the focal delivery of magnetic particle-containing cells that are applicable to a variety of diseases or surgical problems. For example, diseases of blood vessels such as arteries and veins, including atherosclerosis, post-angioplasty restenosis, plaque fracture, thrombosis and vasculitis can be treated by the local delivery of either normal or genetically modified endothelial cells, smooth muscle cells, fibroblasts or other cells to the vessel. For local delivery, a magnet is placed adjacent to the target tissue and magnetic particle-containing cells are delivered. For delivery, cells are either injected directly into the artery at the target tissue or injected upstream of the target tissue and allowed to circulate to the target tissue. If circumferential coverage is required, a mixture of normal and magnetic particle-containing cells can be injected to cover the gravity dependent and independent surfaces, respectively.

The method of the present invention can also be used in the treatment of diseases of the liver including cancers, liver failure or genetic diseases such as LDL receptor deficiency and coagulation factor deficiencies to locally deliver normal or genetically modified endothelial cells, hepatocytes, fibroblasts or other cells to the liver. For local delivery, a magnet is placed adjacent to the area of the liver in which focal delivery is desired. Magnetic particle-containing cells are then delivered either by injection directly into the liver or by injection at a remote site such as the hepatic artery, the portal-venous system, or an organ such as the spleen that empties into the portal venous circulation so that the cells circulate passively or are actively directed via a magnet to the target tissue.

Diseases of the central nervous system, including cancers and neurodegenerative diseases can also be treated by the local delivery of normal or genetically modified neurons, neuroglial cells, endothelial cells, fibroblasts or other cells via the method of the present invention. For delivery, a magnet is placed adjacent to the area of the brain, spinal cord or peripheral nerve into which focal delivery is desired. The magnetic particle-containing cells are then injected directly into the target tissue or at a remote site and allowed to circulate passively to the target tissue or are actively directed to the target tissue by a magnet. Possible remote sites for injection include the ventricular and cerebrospinal fluid system and the circulatory system supplying the nervous system.

The method of the present invention can also be used in the treatment of diseases of the pancreas including cancers and diabetes. The method can be used for local delivery of normal or genetically modified endothelial cells, fibroblasts, pancreatic islet cells or other cells to the pancreas via injection directly to the organ or injection into arteries, veins or lymphatics supplying the pancreas. In this embodiment, prior to administration of the magnetic particle-containing cells, a magnet is placed adjacent to the area of the pancreas to which focal delivery of the cells is desired.

Diseases of the peripheral limbs or of the heart, including those secondary to insufficient blood flow or thrombosis can also be treated by the local delivery of normal or genetically modified endothelial cells, fibroblasts, smooth muscle cells or other cells. Growth is first induced by the local delivery of normal or genetically modified endothelial cells or other cells. A magnet is then placed adjacent to the target tissue. Magnetic particle-containing cells are then injected directly into the target tissue or at a remote site and allowed to circulate passively to the target tissue or actively directed to the target tissue via a magnet. Possible remote sites include arteries, veins and lymphatics supplying the target tissue.

The method of the present invention can also be used in the local delivery of normal or genetically modified endothelial cells, fibroblasts, respiratory epithelial cells or other cells to treat diseases of the respiratory system including cancers and cystic fibrosis. For delivery, a magnet is placed adjacent to the area of the lung into which focal delivery is desired. Magnetic particle-containing cells are then injected directly into the lung or into airways, arteries, veins or lymphatics supplying the lungs.

Diseases of the digestive system including cancers, hemorrhage and ischemia can also be treated by local delivery of normal or genetically modified endothelial cells, epithelial cells, fibroblasts, smooth muscle cells or other cells. For delivery, a magnet is placed outside or within the organ adjacent to the area into which focal delivery is desired. The magnetic particle-containing cells are then injected directly into the target tissue, into the gastrointestinal tract or into arteries, veins or lymphatics supplying the gastrointestinal tract.

The method is also useful in treating diseases of the urogenital system, including cancers and obstructive diseases, by local delivery of normal or genetically modified epithelial cells, endothelial cells, fibroblasts, smooth muscle cells or other cells. For delivery, a magnet is placed outside or within the organ adjacent to the target tissue in which focal delivery is desired. The magnetic particle-containing cells are then injected directly into the target tissue, into the urogenital tract, or into arteries, veins or lymphatics supplying the urogenital system.

What is claimed is:

1. A method of delivering normal or genetically modified cells to a target tissue in an animal comprising:
   (a) inserting magnetic particles into said cells to produce magnetic-particle containing cells;
   (b) administering said magnetic particle-containing cells to the animal; and
   (c) placing a magnetic field around or adjacent to the target tissue to facilitate delivery and attachment of said magnetic particle-containing cells to the target tissue.

2. The method of claim 1, wherein the magnetic particles are administered to the cells by culturing the cells under conditions in which the magnetic particles are internalized.

3. The method of claim 2, wherein the magnetic particles are internalized by phagocytosis.

4. The method of claim 1, wherein the magnetic particles have an average diameter of 4.5 microns.

5. The method of claim 1, wherein the magnetic particles are superparamagnetic.

6. The method of claim 1, wherein said magnetic particle-containing cells are administered by direct injection to the target tissue.

7. The method of claim 1, wherein said magnetic particle-containing cells are administered by injection at a site remote from the target tissue.

8. The method of claim 1 wherein said magnetic particle-containing cells are administered by infusion at the target tissue.

9. The method of claim 8 wherein said infusion is by catheter.

10. The method of claim 1, wherein said magnetic particle-containing cells are selected from the group consisting of neurons, neuroglial cells, endothelial cells, fibroblasts, smooth muscle cells, respiratory epithelial cells, pancreatic islet cells and hepatocytes.

11. The method of claim 1 wherein said target tissue is selected from the group consisting of arteries, veins, lymphatics, liver, spleen, pancreas, heart, urogenital tract, gastrointestinal tract, respiratory system, portal venous system, ventricular fluid system and cerebrospinal fluid system.

12. The method of claim 1 wherein said target tissue is selected from the group consisting of cancerous areas, areas of atherosclerosis, areas of post-angioplasty restenosis, areas of plaque fracture, sites of thrombosis and sites of vasculitis.

13. The method of claim 1, wherein said magnetic particle-containing cells are administered with cells that do not contain magnetic particles.

14. The method of claim 13, wherein both the magnetic particle-containing cells and the cells that do not contain magnetic particles are endothelial cells.

15. The method of claim 13, wherein said magnetic particle-containing cells and cells that do not contain magnetic particles are administered by direct injection.

16. The method of claim 13 wherein said magnetic particle-containing cells and cells that do not contain magnetic particles are administered by infusion.

17. The method of claim 16 wherein said infusion is by catheter.

18. The method of claim 13 wherein the target tissue is selected from the group consisting of cancerous areas, areas of atherosclerosis, areas of post-angioplasty restenosis, areas of plaque fracture, sites of thrombosis and sites of vasculitis.

19. The method of claim 13 wherein the target tissue comprises a luminal surface.

20. The method of claim 19 wherein the target tissue further comprises gravity-dependent and gravity-independent areas.

21. The method of claim 20 wherein the target tissue is placed horizontally and a magnet is placed above the target tissue.

22. The method of claim 21 wherein said target tissue is rotated axially to increase the gravity-dependent area.

* * * * *